United States Patent [19]

Pollock

[11] Plant 4,759

[45] Aug. 18, 1981

[54] CAMOTE PLANT

[76] Inventor: Steven H. Pollock, 6738 Spring Brook, San Antonio, Tex. 78249

[21] Appl. No.: 56,772

[22] Filed: Jul. 11, 1979

[51] Int. Cl.[3] ..... A01H 15/00

[52] U.S. Cl. ..... Plt./89

[58] Field of Search ..... Plt./89

*Primary Examiner*—Robert E. Bagwill

[57] ABSTRACT

A new and distinct camote plant has been discovered. The novel psychotropic plant is a variety of the subtropical terricolous Basidiomycete fungus *Psilocybe tampanensis.*

2 Drawing Figures

1

The present invention relates to a new and distinct variety of camote plant. Field research by the applicant in the Sierras of northeastern Oaxaca has revealed that Mazatecs refer to large sclerotia of the sacred psychoactive derrumbe (landslide) fungus *Psilocybe caerulescens* Murrill in Spanish as camote (sweet potato) or camote del hongo (sweet potato of the mushroom) and in their own language as n'o tsé. *P. caerulescens* does not produce sclerotia in cultivation under any conditions observed to date.

The applicant's new camote plant is a variety of a recently described psychotropic Basidiomycete, *Psilocybe tampanensis* Guzmán & Pollock. The wild fungus is a subtropical terricolous species [Guzmán & Pollock, Mycotaxon 7 (2):373–376 (July-September, 1978)]. The type specimen, a solitary carpophore, was collected by the applicant during the Second International Mycological Congress at Tampa, Fla. during the summer of 1977. No other wild collections are known.

The applicant discovered the new camote plant as a sector of a pure culture of *Psilocybe tampanensis* grown on ryegrass seed medium used as spawn for fructification studies of *P. tampanensis* in San Antonio, Bexar County, Tex. The applicant had previously developed ryegrass seed medium for Psilocybe and Panaeolus spawn production. Details of the preparation of ryegrass seed medium and various other novel media are described by the applicant in his book *Magic Mushroom Cultivation* (Herbal Medicine Research Foundation; San Antonio, Tex., 1977).

The novel camote plant was cloned by tissue culture of medullary plectenchymal cells on 1.5% MEA (malt extract agar) and asexually propagated by mycelial transfers. On MEA cloned mycelia of the camote plant vary from white to yellow and brown [e.g. color 84. s. Y (strong yellow) and 57. l. Br (light brown) from *ISCC-NBS Color-Name Charts Illustrated with Centroid Colors* (*Supplement to NBS Circular* 553)] but sometimes turn blue from oxidation of an indole metabolite. On potato-dextrose agar or potato-dextrose-yeast agar the mycelia tend to be more strongly pigmented. Similar color characteristics have been observed for typical *tampanensis* strains of mycelia that do not produce sclerotia. Occasionally small sclerotia (usually less than 5 mm. or rarely up to 1 cm. in diameter) are produced on agar media by the cloned camote plant, distinguishing it

2 from typical *tampanensis* strains of mycelia that do not produce sclerotia.

Asexual reproduction of the novel camote plant has been accomplished many times by the applicant using ryegrass seed media in San Antonio, Bexar County, Tex. At temperatures in the range of 25°–30° centigrade in darkness or in an illuminated area camote primordia form on the walls of the glass container and in the media in about three weeks to a month after inoculation of ryegrass seed medium and mature in about three months after inoculation. They tend to grow larger if not harvested until six to eight months after inoculation.

Figure 1:
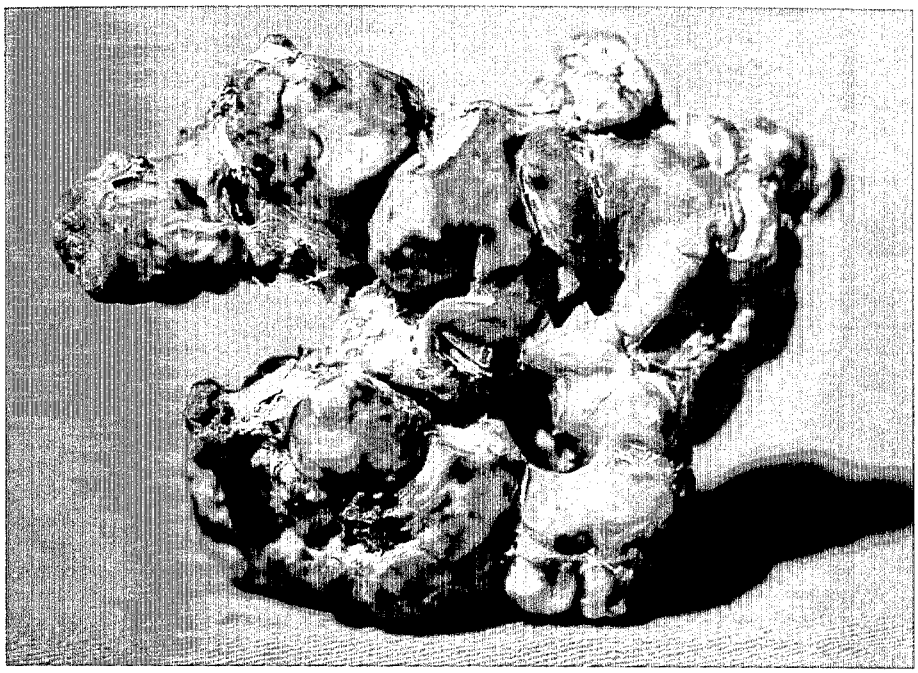
FIG. 1 is a pictorial view of the new and distinct variety of camote plant.

Camotes tend to become highly irregular in shape. The camote photographed in frontal view in FIG. 1 grew for five months against the side of a 1½ pint glass container of ryegrass seed medium. Measurements of this specimen when harvested were the following: weight 22.5 g., length (max.) 5.4 cm., width (max.) 3.2 cm. and height (max.) 4.2 cm. After the specimen was completely air dried at 4° C., its measurements were recorded as follows: weight 7.4 g., length (max.) 4.3 cm., width (max.) 2.2 cm. and height (max.) 3.2 cm.

Figure 2:
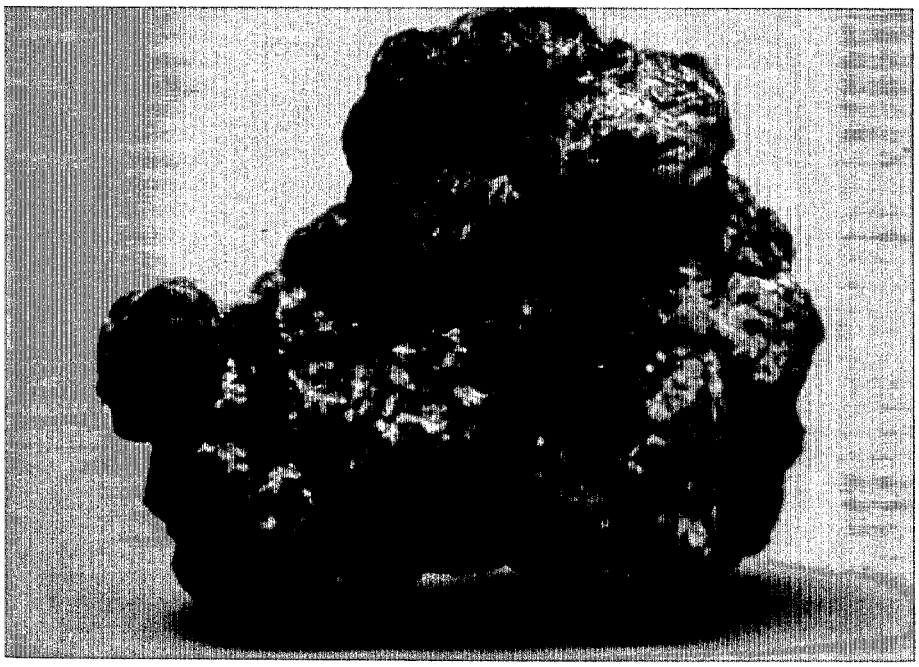
FIG. 2 is a pictorial view of a larger, older specimen of the new camote plant.

The camote photographed in FIG. 2 grew for seven months in ryegrass seed medium in a 1½ pint glass container. Measurements of this robust specimen at harvest were the following: weight 44.6 g., length (max.) 6.1 cm., width (max.) 5.6 cm. and height (max.) 5.7 cm. After air drying at 4° C., the camote measurements were recorded as follows: weight 8.3 g., length (max.) 3.9 cm., width (max.) 3.4 cm. and height (max.) 3.5 cm.

Camote medullary tissue is generally creamy white, whereas cortical tissue is light yellowish brown and rind tissue tends to be more strongly pigmented. Both browning and bluing oxidative phenomena occur in all tissues of the new camote plant. Therefore, coloration tends to be highly variable, often with numerous hues of brown, yellow, orange, blue, violet, green and white. Some examples of rind colors are the following "Centroid Colors": 54. br O (brownish orange), 57. l. Br (light brown), 74. s. y Br (strong yellowish brown), 84. s. Y (strong yellow), 179 deep B (deep blue), 194 v. p B (vivid purplish blue), 197 deep p B (deep purplish blue) and 208 deep V (deep violet).

The instant camote plant produces abundant carpophores when spawn is cased. Optimum diurnal temperatures for fructification are in the range of 32° centigrade (daytime) and 21° centigrade (night). Carpophores usually fail to mature and do not sporulate under incandescent or fluorescent light. In greenhouse conditions the instant plant produces normal fruit bodies that sporulate copiously. A mycological description of the sporocarp follows in which "Centroid Colors" are indicated in brackets.

The pileus expands to between 8 and 38 mm. in diameter, is papillate to convex or slightly umbilicate, smooth, subviscid to viscid when moist, hygrophanous, ochraceous brown to straw brown [e.g., 75 deep y Br (deep yellowish brown), 77 m. y Br (moderate yellowish brown) and 76 l. y Br (light yellowish brown)] when mature, sometimes brownish pink [e.g., 33 br Pink (brownish pink)] when immature, and slightly bluish at the margin. Lamallae are subadnate and dark brown with a violet hue [211 m. V (moderate violet)] with whitish edges. The stipe varies from about 1 to 5 mm. in width, has been recorded up to 60 mm. in length, is fibrous, slightly thickened at the base, smooth but subflocculose at the apex, yellowish brown to reddish brown [e.g., 77 m. y Br (moderate yellowish brown) and 42 l. r Br (light reddish brown)], with whitish to cesious base [e.g., 180 v. l. B (very light blue)]. Flesh is whitish to yellowish, thin, oxidizing to blue [178 s. Blue (strong blue)] when traumatized. Odor and taste are farinaceous. The spore print is dark brown [59 d. Br (dark brown)] with a violaceous hue [208 deep V (deep violet)].

Spores are (7.7–) 8.8–9.9 (–12)×(6–) 7–8.8 (–9.9)×5-.5–6.6 μm, subrhombic in face view, subelliptic in side view, yellowish brown [74 s. y Br (strong yellowish brown)] in KOH, with a thick smooth wall, a distinct germ pore and a short appendage. Basidia are 14–22-×8–10 μm, tetrasporic, hyaline, vesiculose or subclaviform. Pleurocystidia are absent. Cheilocystidia are 16–22×4–9 μm, lageniform, with a somewhat flexuous long neck 2.2–3 μm in diameter, sometimes irregularly branched, hyaline, abundant, forming a sterile band at the edge of the gill. Subhymenium is hyaline in KOH but with yellow brown pigment irregularly incrusted on the walls. Trama is regular, light brown to dark yellowish brown, with diffuse pigment; hyphae are 10 μm in diameter. The epicutis is subgelatinized, consisting of parallel, thin (about 2 μm wide), hyaline hyphae. The hypodermium is formed by pigmented to hyaline, elongated to subglobose hyphae. Clamp connections are present.

In addition to their value as recreational euphoriants, psychotropic camote plants have great potential as psychotherapeutic medicaments.

What is claimed is:

1. A new and distinct variety of camote plant substantially as shown and described.

* * * * *